(12) United States Patent
Kurahashi

(10) Patent No.: US 7,317,822 B2
(45) Date of Patent: Jan. 8, 2008

(54) IMAGE FILE CONTROL APPARATUS, A CONTROL METHOD OF THE IMAGE FILE, AND A RECORDING MEDIUM

(75) Inventor: Akira Kurahashi, Hachioji (JP)

(73) Assignee: Konica Minolta Holdings Inc., Tokyo (JP)

( * ) Notice: Subject to any disclaimer, the term of this patent is extended or adjusted under 35 U.S.C. 154(b) by 738 days.

(21) Appl. No.: 10/785,530

(22) Filed: Feb. 23, 2004

(65) Prior Publication Data

US 2004/0170310 A1    Sep. 2, 2004

(30) Foreign Application Priority Data

Feb. 28, 2003    (JP) .............................. 2003-052594

(51) Int. Cl.
*G06K 9/00*    (2006.01)
(52) U.S. Cl. ..................... 382/132; 382/128; 378/37
(58) Field of Classification Search ................ 382/128, 382/129, 130, 131, 132, 133, 134; 378/37; 600/300; 128/915, 920, 922; 250/370.09, 250/492.1
See application file for complete search history.

(56) References Cited

U.S. PATENT DOCUMENTS 6,137,860 A * 10/2000 Ellegood et al. .............. 378/58
6,851,851 B2 * 2/2005 Smith et al. ................. 378/189
6,934,409 B2 * 8/2005 Ohara ......................... 382/132

FOREIGN PATENT DOCUMENTS

JP    2001-238871 A    9/2001

* cited by examiner

*Primary Examiner*—Samir Ahmed
*Assistant Examiner*—Abolfazl Tabatabai
(74) *Attorney, Agent, or Firm*—Frishauf, Holtz, Goodman & Chick, P.C.

(57) ABSTRACT

An image file control method for storing plural sets of image data wherein each of plural sets of image data is obtained in such a way that a body part of a patient having an ID code is radiographed with a magnification by an absorption contrast radiography or a phase contrast radiography so as to obtain a radiation image of the body part and the radiation image is read with a reading sampling pitch by an image reading device so that the image reading device outputs raw image data of the body part; comprising step of; storing plural sets of raw image data by attaching supplemental information to each of plural sets of raw image data, wherein the supplemental information contains an ID code of a patient and at least one of a set of a magnification and the reading sampling pitch and a full size sampling pitch calculated from the set of the magnification and the reading sampling pitch.

6 Claims, 2 Drawing Sheets

IMAGE FILE CONTROL APPARATUS, A CONTROL METHOD OF THE IMAGE FILE, AND A RECORDING MEDIUM

BACKGROUND OF INVENTION

The present invention is concerned in an image file control apparatus, a control method of the image file, and a recording medium, particularly relates to the image file control apparatus by which the image file obtained by a phase contrast image photographing is controlled, relates to the control method of the image file, and relates to a recording medium in which a program to conduct the control method of the image file is recorded.

Generally, a radiation image photographing apparatus for which an action by which the radiation transmits the material is utilized, is widely used in a medical image diagnosis or non-destructive inspection. Particularly, about the radiation image apparatus for the mammography which is used for the photographing of the specific part, normally, a method by which a subject is fixed on a subject table integrated with a detection member of the radiation image and photographed, is conducted. Then, when the image data obtained by the photographing is outputted as an image, by the radiation image photographing apparatus or an image output apparatus, a size is converted so as to correspond to the resolving power of each image output apparatus, or the size is converted so as to be the magnification required by an observer, and the image data is controlled.

However, although the subject is photographed in the full size dimension by the above-described photographing method, the contrast of the image is not sufficiently increased, and there is a problem that the visibility of the image is insufficient as a medical use photographing apparatus which is used for reading a fine structure of the specific part of the human body.

Accordingly, conventionally, a method by which, by using a radiation tube used in a general medical institution (a small focal point radiation source of a focal point size 30-300 μm), the phase contrast image is obtained, is widely known (for example, refer to Patent Document 1). According to this, comparing to the image of only an ordinary absorption contrast, the contrast of the boundary of the subject can be drawn high, and more clear and highly fine radiation image can be obtained. Hereupon, in order to obtain such a phase contrast image, it is necessary that a predetermined distance is provided between the subject and the radiation image information detection member. Further, when considering the viewpoint in which the burden of the subject is lightened in the medical job site, and the cost for the equipment, it is desirable that both of, not only "phase image photographing mode" to photograph the phase contrast image, but also "normal photographing mode" to photograph the image of only an ordinary absorption contrast, can be conducted by the same radiation image photographing apparatus.

Herein, at the time of photographing in the phase image photographing mode, because an interval is provided between the subject and the radiation image information detection member, the radiation which projects the subject is diffused to the radiation image information detection member, and a field of irradiation is spread. That is, the image obtained in the phase image photographing mode, is enlarged more than the case where the same part is photographed in the normal photographing mode.

However, when the image data obtained in the phase image photographing mode is to be controlled in the same manner as in the normal photographing mode, the contradiction is generated from the difference of the magnification ratio. As one of means for solving this, a method by which the image data obtained by the phase image photographing mode is converted into, for example, the full size so that it becomes the same size as the image data obtained by the normal photographing mode, and controlled, is listed. However, in the image data, it is general that the conversion of the resolving power of the image output apparatus is required at the time of the output of the image, and it is required corresponding to the magnification ratio which is necessary for the observer, and in this method, on the image data obtained by the phase image photographing mode, the resolving power conversion is repeatedly conducted. In this manner, when the resolving power conversion is repeatedly conducted, in the image data, corresponding to the conversion of the resolving power, each time, the data is thinned out or supplemented, and results in deterioration. When the number of times of the conversion of the resolving power is many, a possibility that the deterioration advances by the amount, resulting in the image of the low image quality, is high.

SUMMARY OF THE INVENTION

The object of the present invention is to intend the decrease of the deterioration of the image data, even when the image data obtained by the phase image photographing mode and the normal photographing mode exist in the mixture, by effectively controlling the image data.

The invention written in an item 1 is An image file control apparatus for storing plural sets of image data, wherein each of plural sets of image data is obtained in such a way that a body part of a patient having an ID code is radiographed with a magnification by an absorption contrast radiography or a phase contrast radiography so as to obtain a radiation image of the body part and the radiation image is read with a reading sampling pitch by an image reading device so that the image reading device outputs raw image data of the body part; comprising; a step of storing plural sets of raw image data by attaching supplemental information to each of plural sets of raw image data, wherein the supplemental information contains an ID code of a patient and at least one of a set of a magnification and the reading sampling pitch and a full size sampling pitch calculated from the set of the magnification and the reading sampling pitch. the set of the magnification and the reading sampling pitch.

The invention written in an item 2 is characterized in that: in the image file control apparatus written in an item 1, further comprising of; a resolving power converting device to convert the raw image data stored in the recording device into a predetermined resolving power; wherein the resolving power converting device calculates the magnification and reduction ratio from the full size sampling pitch.

The invention written in an item 3 is characterized in that: in the image file control apparatus written in an item 2, wherein the resolving power converting device makes the full size sampling pitch correspond to a predetermined resolving power, when the raw image data is converted into a predetermined resolving power.

The invention written in an item 4 is characterized in that: in the image file control apparatus written in an item 3, wherein the resolving power converting device converts the raw image data based on the magnification and reduction ratio calculated so as to be the predetermined resolving power, and the memory apparatus stores the converted raw image data.

The invention written in an item 5 is characterized in that: in the image file control apparatus written in an item 4, wherein the resolving power converting device converts the raw image data based on the magnification reduction ratio calculated so as to be the resolving power in which the magnification ratio becomes a full size.

The invention written in an item 6 is characterized in that: in the image file control apparatus of any one of items 1-5, wherein to an image output device to output the raw image data in the recording device.

The invention written in an item 7 is characterized in that: in the image file control apparatus written in the item 6, wherein the resolving power converting device converts the raw image data based on the magnification reduction ratio calculated so as to be the resolving power which is required by the image output device.

The invention written in an item 8 is characterized in that: in the image file control apparatus written in the item 6 or 7, wherein the resolving power converting device converts the raw image data based on the magnification reduction ratio calculated so as to be the resolving power which is required by the image output device.

The invention written in an item 9 is characterized in that: in the image file control apparatus written in any one of items 6-8, wherein the resolving power converting device converts the raw image data based on the magnification and reduction ratio calculated so as to be a predetermined resolving power, before the output of the data outputting device.

The invention written in an item 10 is characterized in that: in the image file control apparatus written in any one of items 6-8, wherein the resolving power converting device converts the raw image data based on the magnification and reduction ratio calculated so as to be a resolving power in which the magnification becomes a full size before the output of the data outputting device.

The invention written in an item 11 is characterized in that: in the image file control apparatus written in any one of items 6-8, wherein the resolving power converting device converts the raw image data based on the magnification and reduction ratio calculated so as to be a resolving power that is required by the image outputting device, before the output of the data output device.

The invention written in an item 12 is An image file control method for storing plural sets of image data, wherein each of plural sets of image data is obtained in such a way that a body part of a patient having an ID code is radiographed with a magnification by an absorption contrast radiography or a phase contrast radiography so as to obtain a radiation image of the body part and the radiation image is read with a reading sampling pitch by an image reading device so that the image reading device outputs raw image data of the body part; comprising step of; storing plural sets of raw image data by attaching supplemental information to each of plural sets of raw image data, wherein the supplemental information contains an ID code of a patient and at least one of a set of a magnification and the reading sampling pitch and a full size sampling pitch calculated from the set of the magnification and the reading sampling pitch.

The invention written in an item 13 is characterized in that: in the image file control method written in the item 12, wherein the raw image data is converted into a predetermined resolving power, and the magnification and reduction ratio at the time of the conversion is calculated from the full size sampling pitch.

The invention written in an item 14 is characterized in that: in the image file control method written in the item 13, wherein the raw image data is converted based on the magnification and reduction ratio calculated so as to be a predetermined resolving power, at the time of conversion of the raw image data.

The invention written in an item 15 is characterized in that: in the image file control method written in the item 14, wherein the raw image data is converted based on the magnification and reduction ratio calculated so as to be the resolving power in which the magnification becomes a full size, at the time of conversion of the raw image data.

The invention written in an item 16 is characterized in that: in the image file control method written in any one of the items 14-15, further comprising step of: outputting the raw image data to an image output device.

The invention written in an item 17 is characterized in that: in the image file control method written in the item 16, wherein the raw image data is converted based on the magnification and reduction ratio calculated so as to be the resolving power which is required by the image output device, at the time of conversion of the raw image data.

The invention written in an item 18 is characterized in that: in the image file control method written in the item 16 or 17, wherein the raw image data is outputted together with also the accompanying information, when the raw image data is outputted to the image output device.

A recording medium records a program to control a computer to function as a storing plural sets of image data, wherein each of plural sets of image data is obtained in such a way that a body part of a patient having an ID code is radiographed with a magnification by an absorption contrast radiography or a phase contrast radiography so as to obtain a radiation image of the body part and the radiation image is read with a reading sampling pitch by an image reading device so that the image reading device outputs raw image data of the body part; comprising; a step of storing plural sets of raw image data by attaching supplemental information to each of plural sets of raw image data, wherein the supplemental information contains an ID code of a patient and at least one of a set of a magnification and the reading sampling pitch and a full size sampling pitch calculated from the set of the magnification and the reading sampling pitch.

The invention written in an item 20 is characterized in that: in the recording medium written in the item 19, wherein the raw image data is converted into a predetermined resolving power, and the magnification and reduction ratio calculated from the full size sampling pitch at the time of conversion.

The invention written in an item 21 is characterized in that: in the recording medium written in the item 20, wherein the raw image data is converted based on the magnification and reduction ratio calculated so as to be a predetermined resolving power, at the time of conversion of the raw image data.

The invention written in an item 22 is characterized in that: in the recording medium written in the item 21, wherein the raw image data is converted based on the magnification and reduction ratio calculated so as to be the resolving power in which the magnification becomes a full size, at the time of conversion of the raw image data.

The invention written in an item 23 is characterized in that: in the recording medium written in any one of the items 19-22, further comprising of: a program to control a computer to function as a outputting the raw image data to the image output device.

The invention written in an item 24 is characterized in that: in the recording medium written in the item 23, wherein the raw image data is converted based on the magnification and reduction ratio calculated so as to be the resolving power, which is required by the image output device, at the time of conversion of the raw image data.

The invention written in an item 25 is characterized in that: in the recording medium written in the item 23 or 24, wherein the raw image data is outputted together with also the accompanying information, when the raw image data is outputted to the image output device.

DETAILED DESCRIPTION OF THE PREFERRED EMBODIMENT

Figure 1:
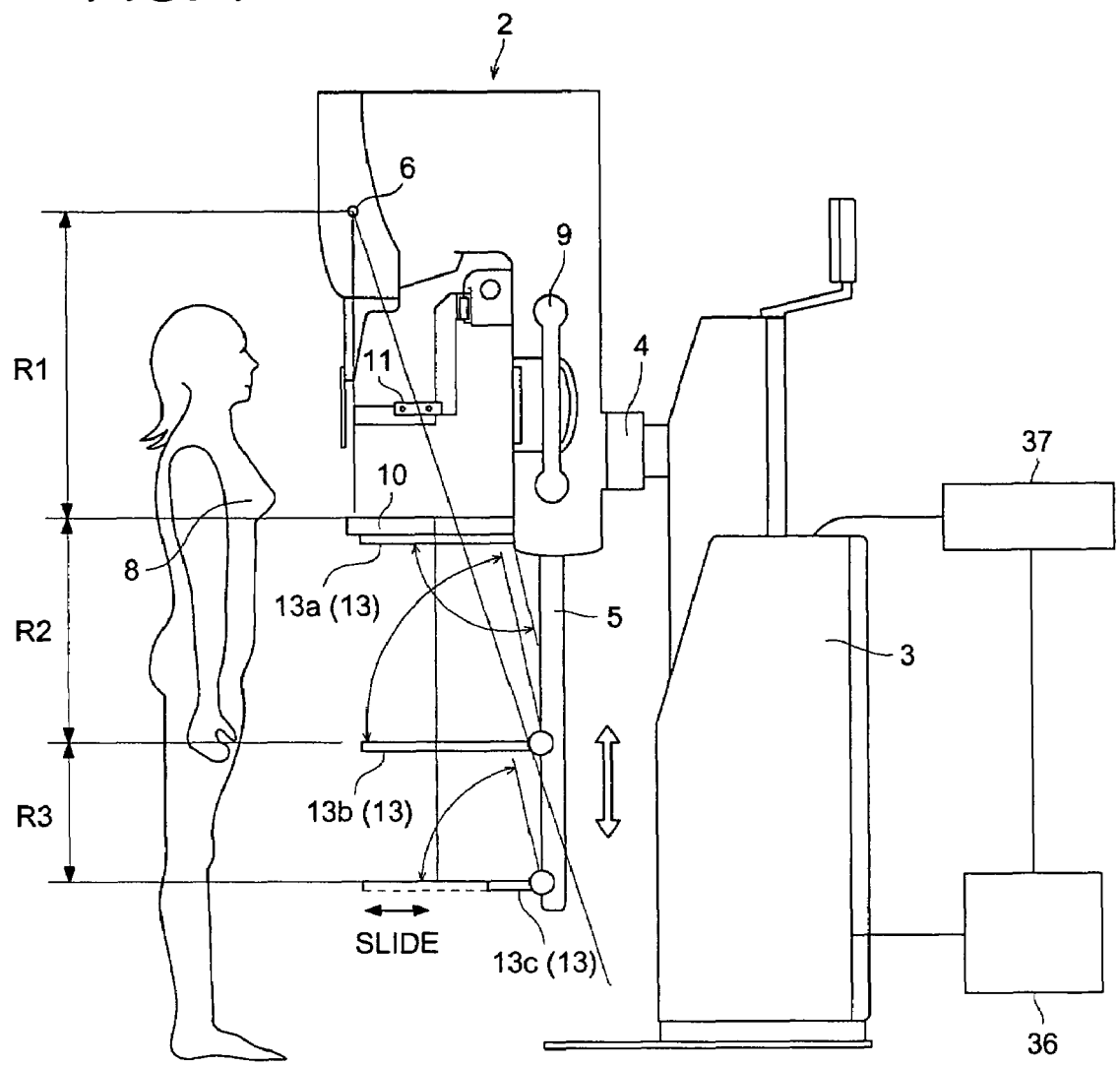
FIG. 1 is a side view of a radiation image photographing apparatus according to the present invention.

Referring to the attached drawings, the embodiment of the present invention will be described below. In the present embodiment, referring to FIG. 1, a case where an image file control method of the present invention is applied for an image file obtained in a radiation image photographing apparatus, will be described. FIG. 1 is a side view of a radiation image photographing apparatus 1.

The radiation image photographing apparatus 1 functions as an image input apparatus by which the image data photographed by an absorption contrast image or phase contrast image photographing is made. In this radiation image photographing apparatus 1, a photographing section 2 is supported by a support shaft 4 provided to a support base 3, and is attached to a support member 5 so that it can be moved upward and downward in a predetermined range along a guide rail, not shown, provided to the support member 5 by a drive apparatus, not shown. To the support base 3, a radiation operation panel 37 having keys which conduct the selection of a photographing mode is connected, and further, a power supply 36 which is a power source of the apparatus, is connected.

On the upper portion of the photographing section 2, a radiation source 6 to irradiate the radiation is provided, and as the radiation source 6, an X-ray tube whose focal point is 30-3000 μm which is used in a general medial institution, is used. In detail, the radiation tube which irradiates the radiation whose wavelength is about 1 Å, is used. In this radiation tube, when an electron generated by the thermal excitation is accelerated by the high voltage, and made to collide with a cathode, and its kinetic energy is converted into the radiation energy, the radiation is irradiated.

Herein, the focal point of the radiation is, for example, a window viewed from the subject direction from which the radiation generated when the electron comes into collision with a rotated anode of the radiation tube, is taken out. Generally, this is a square and the length of its side is a focal point size. When the shape of the focal point is a circle, the focal point size indicates its diameter, and when it is a rectangle, the focal point size indicates its short side. As the measurement method of this focal point size, a method by a pin-hole camera and a method using a micro test chart are written in JIS Z 4704. Normally, as the focal point size, a value according to the measurement of the radiation tube manufacturer is shown in the product specification.

On both side surfaces of the photographing section 2, a grip bar 9 for supporting a body of the subject is provided, and further, at a position which is under the radiation source 6, and vertically extending from the radiation source 6, a subject table 10 for supporting the subject 8 from below and a pressure plate 11 for pressing the subject 8 from above, and fixing it, are arranged in such a manner that they can elevate. Hereupon, it is preferable that the subject table 10 is a table formed of a square frame, or on which a transparent thin plastic plate is adhered.

In the present embodiment, to a supporting member 5, a plurality of detection member supporting tables 13 are attached at a position which is below the subject table 10 and a position which is almost vertically extending from the radiation source 6, in such a manner that they are opposed to the radiation source 6. Further, a radiation image information detection member 23 (refer to FIG. 2) as a means for detecting the radiation image information according to the radiation transmitted through the subject 8 is detachably mounted on each of detection member support tables 13. The radiation image information detection member 23 has an area necessary for detecting the radiation transmitted through the subject 8, and the radiation irradiated from the radiation source 6 transmits through the subject 8 and is observed as the radiation energy (radiation image information) by the radiation image information detection member 23.

Then, in the plurality of detection member support table 13, when the absorption contrast image is photographed, there is a support table for absorption image 13a which supports the radiation image information detection member 23 in such a manner that it comes into close contact with the lower surface of the subject table 10, and when the phase contrast image is photographed, there are phase image support tables 13b and 13c, which support the radiation image information detection member 23 spaced with a predetermined interval from the subject table 10, in such a manner that at least one part of the radiation image information detection member 23 is arranged in the radiation field of the radiation source 6.

These absorption image support table 13a and phase image support tables 13b and 13c face to the subject table 10 when it is used, by a support table drive source 24 (refer to FIG. 2), and when it is waiting, it is rotated around a base end portion, and a leading edge portion is approached to the support member 5, and is a tilt able type so that it takes refuge out of the radiation field.

Then, in the present embodiment, for example, the absorption image support table 13a is arranged on the lower surface of the subject table 10 arranged at a position (R1) separated by 55-70 cm from the radiation source 6, and at a position (R2) separated by the distance of 0.5-1.5 times of R1 from the subject table 10, the phase image support table 13b is arranged, and further, under it, the phase image support table 13c is arranged at a position (R3) separated by the distance of 0.3-1.0 times of R1.

To the radiation image information detection member 23, a grid (not shown) for shutting the scattering ray is provided for the purpose of preventing that the scattering ray from the radiation source 6 influences on the photographing, however, because, as the distance from the subject 8 is increased, an amount of the scattering ray is decreased, and the influence on the photographing is also decreased, the radiation image information detection member 23 attached to the phase image support tables 13b, and 13c may be one which does not have the grid.

Figure 2:
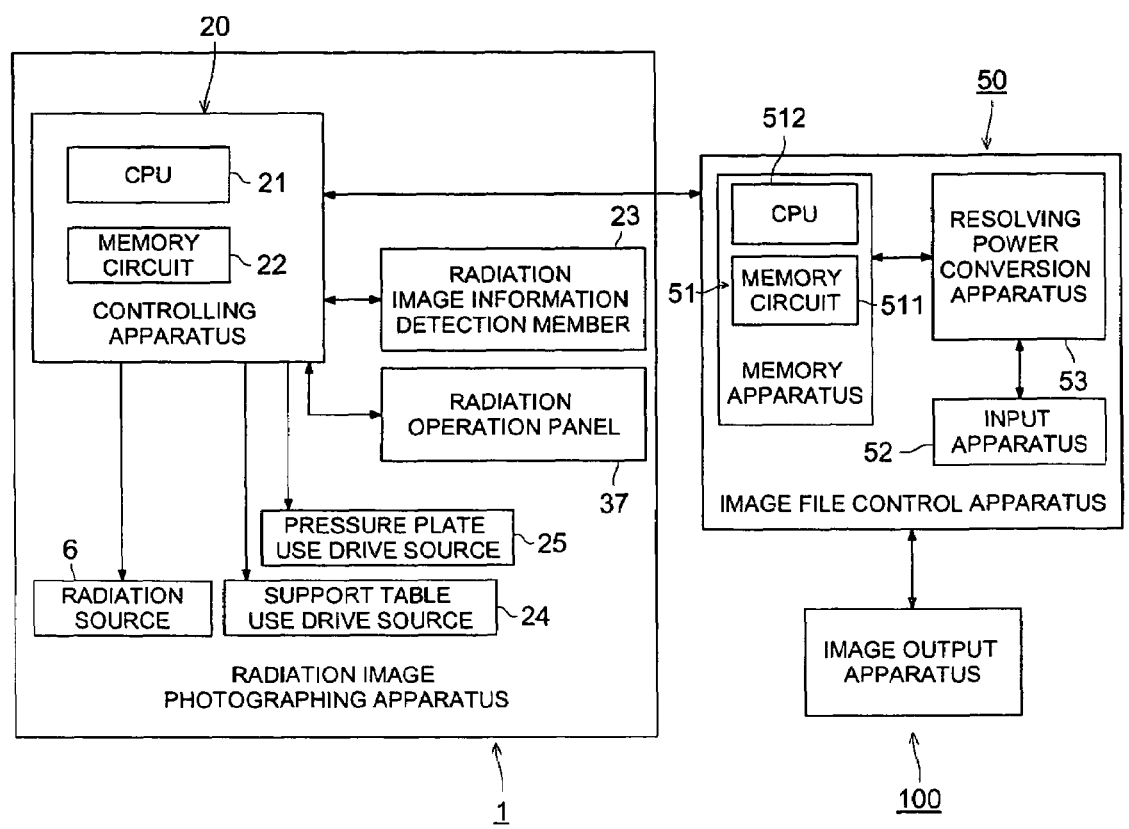
FIG. 2 is a block diagram expressing a main controlling structure of the radiation image photographing apparatus of FIG. 1.

Further, in the radiation image photographing apparatus 1 in the present embodiment, as shown in FIG. 2, a controlling apparatus 20 for controlling each section is provided. The controlling apparatus 20 is structured by a memory circuit 22, and a CPU 21, and controls each kind of equipment connected to an interface according to a controlling program written in the memory circuit 22 or controlling data. To this controlling apparatus 20, a pressure plate use drive source 25 of the pressure plate 11, support table use drive source 24 of the detection member support table 13, a radiation operation panel 37 for inputting the photographing mode, radiation source 6, and radiation image information detection member 23 are connected.

On the radiation operation panel 37, keys which can select a "normal photographing mode" which is conducted by equipping the radiation image information detection member 23 on the absorption image use support table 13a, a "first phase photographing mode" which is conducted by equipping the radiation image information detection member 23 on the phase image use support table 13b, and a "second phase photographing mode" which is conducted by equipping the radiation image information detection member 23 on the phase image use support table 13c, are provided, and the "normal photographing mode" corresponding to the detection member support table 13 and a plurality of "phase image photographing modes" whose magnification is different, can be selectively inputted. Hereupon, as the radiation operation panel 37, an input apparatus in which a keyboard is used, or a magnetic card, bar code, and HIS (In-Hospital Information System) are used, may be separately provided from the radiation operation panel 37.

The CPU 21 develops a program specified in each kind of programs stored in the memory circuit 22 into an operation area in the memory circuit 22, and corresponding to the input signal from each section, conducts each kind of processing according to the program.

Then, to the controlling apparatus 20, an image file control apparatus 50 which controls the image file is connected. The image file control apparatus 50 reads the accompanying information from the image file, and size-converts the image data so that it corresponds to a predetermined resolving power. In the image file control apparatus 50, a memory apparatus 51 which stores the image file and an input apparatus 52 into which an arbitrary resolving power is inputted, and a resolving power conversion apparatus 53 which converts the image data in the file based on the inputted resolving power in the input apparatus 52, are provided.

The memory apparatus 51 is structured by a memory circuit 511 which stores each kind of data and programs inputted from the controlling apparatus 20 of the radiation image photographing apparatus 1, and a CPU 512 for conducting the program stored in the memory circuit 511, and controls each kind of equipment connected to the interface (data output apparatus) according to the control program or control data written in the memory circuit 511.

In detail, the memory circuit 511 stores the image data and the image file having the accompanying information attached to this image data, and together with that, a program for controlling the image data obtained in the normal photographing mode, first phase photographing mode, and second phase photographing mode is recorded in it. That is, the memory apparatus 51 functions as the recording medium in the present invention.

The image data is the radiation image information inputted from each radiation image information detection member 23, and the accompanying information is the information relating to this image data. As the accompanying information, the kind of the photographing mode when the image data is obtained, reading sampling pitch at the time of the image reading, and magnification at the time of photographing, are listed. Herein, a sampling pitch means a resolving power when the image data is obtained or outputted, or a pixel interval.

Then, when the object 8 is photographed in each photographing mode, because the interval between each radiation image information detection member 23 and the subject table 10 is different, the radiation field in each radiation image information detection member 23 is different, and the magnification of the obtained image is different for each photographing mode. Therefore, for each radiation image information detection member 23, the reading sampling pitch is determined corresponding to its magnification.

For example, in the case of the present embodiment, when the mode is the normal photographing mode, because the radiation image information detection member 23 is arranged just below the subject table 10, the image is photographed in the full size largeness, and the magnification at the time and the reading sampling pitch are stored as the accompanying information. Further, when it is the first phase photographing mode, because the radiation image information detection member 23 is arranged at a position separated by R2 from the subject table 10, the image is photographed in the magnification of (R1+R2)/R1 as compared to the full size largeness, and the magnification at the time and the reading sampling pitch are stored as the accompanying information. Then, when it is the second photographing mode, because the radiation image information detection member 23 is arranged at a position separated by (R2+R3) from the subject table 10, the image is photographed in the magnification of (R1+R2+R3)/R1 as compared to the full size largeness, and the magnification at the time and the reading sampling pitch are stored as the accompanying information.

Then, the image data stored in the memory apparatus 51 is converted by the resolving power conversion apparatus 53 based on a predetermined resolving power inputted from the input apparatus 52 and the accompanying information. When the magnification and reduction ratio at the time of this conversion is calculated, the resolving power conversion apparatus 53 calculates the full size sampling pitch based on the magnification at the time of photographing and the reading sampling pitch which are stored in the accompanying information. Then, the resolving power conversion apparatus 53 calculates the magnification and reduction ratio from a predetermined resolving power and the full size sampling pitch inputted from the input apparatus 52. Hereupon, the resolving power conversion apparatus 53 can convert the image data into a predetermined resolving power also in any case where the image file is inputted from the radiation image photographing apparatus 1 into the image file control apparatus 50, where the image file is stored in the memory apparatus 51, or where the image file is outputted to the image output apparatus 100.

When a predetermined resolving power is inputted from the input apparatus 52, any one of the resolving power required by the image output apparatus, the resolving power in which the magnification at the time of photographing becomes a full size, or an arbitrary resolving power, is selected. Specifically, when the resolving power required by the image output apparatus is selected, the image data can be controlled under the condition that the image data is converted so as to correspond to the resolving power required by the image output apparatus. Herein, the resolving power required by the image output apparatus is determined by the resolving power of the image output apparatus 100, the pixel interval or the display magnification needed by the observer.

Further, when the resolving power in which the magnification at the time of photographing becomes a full size, is selected, the image data can be controlled under the condition that the image data is converted so as to correspond to the resolving power in which the magnification at the time of photographing becomes a full size. Then, when an arbitrary resolving power is selected, the image data can be controlled under the condition that the image data is converted so as to correspond to an arbitrary resolving power.

To this image file control apparatus 50, an image output apparatus 100 such as a printer to output the image or a display is connected. The image output apparatus 100 displays the image data when the image file is inputted from the interface of the memory apparatus 51.

Next, while the specific procedure of the photographing by the radiation image photographing apparatus 1 in the present embodiment is described, the control method of the image file will be described.

Initially, the operator attaches the radiation image information detection member 23 to a detection member support table 13, and from the radiation operation panel 37, the photographing mode is selected by the key.

Based on this selection, the controlling apparatus 20 controls a support table use drive source 24 in such a manner that the detection member support table 13 to which the radiation image information detection member 23 is attached, faces the subject table 10, and the detection member support table 13 other than them is made to take refuge in the out of the radiation field of the radiation source 6.

After that, when a tested subject puts the subject 8 on the subject table 10, the controlling apparatus 20 lowers the pressure plate 11 by controlling the pressure plate drive source 25, press the subject 8 and irradiates the radiation from the radiation source 6, and conducts the radiation image photographing. In this case, the controlling apparatus 20 finds the magnification at the time of photographing and the reading sampling pitch at the time of the reading, and this is made the accompanying information of the image data obtained by the photographing and relates that to the image data, and outputs to the image file control apparatus 50.

The image file control apparatus 50 makes the image file from the image data and the accompanying information and stores it. Herein, when a predetermined resolving power is inputted from the input apparatus 52, the resolving power conversion apparatus 53 converts the image data based on the predetermined resolving power and the accompanying information of the image file, and stores it, and stores a predetermined resolving power and magnification and reduction ratio, at the time of conversion.

For example, when the resolving power required by the image output apparatus is selected as a predetermined resolving power by the input apparatus, the resolving power conversion apparatus 53 reads the magnification and reading sampling pitch stored as the accompanying information, and calculates the full size sampling pitch. Then, the resolving power conversion apparatus 53 calculates the magnification and reduction ratio from the full size sampling pitch and the inputted resolving power, and based on this magnification and reduction ratio, reduces and enlarges it by the well known method and stores it. Then, as the accompanying information of the converted image data, the resolving power and magnification and ratio at the time of conversion are stored.

Hereupon, when the predetermined resolving power is finer than the full size sampling pitch, a insufficient part of the image data is supplemented by the well known method and made to correspond to the predetermined resolving power.

Then, when the image file is displayed, the image output apparatus 100 reads the image file from the image file control apparatus 50, and the image data is displayed as the image.

As described above, according to the present embodiment, when the memory apparatus 51 stores the image data, because it stores the magnification at the time of photographing and the reading sampling pitch at the time of image reading as the accompanying information, when this accompanying information is made the standard at the time of conversion of the image data, even when many times of size conversion are not conducted, the image can be displayed in an intended size and resolving power. As in this manner, because the number of times of the size conversion of the image data can be suppressed, the deterioration of the image data can be reduced.

Then, even when the image data obtained in each of the absorption contrast image photographing (normal photographing mode) and the phase contrast image photographing (phase image photographing mode) are mixed, because the magnification at the time of photographing and the reading sampling pitch at the time of image reading are stored as the accompanying information, the image data obtained by the different photographing method can be controlled in the same manner, and the control of the image file can be effectively conducted.

Hereupon, it is of course that the present invention can be appropriately changed without being limited to the above embodiment. For example, in the present embodiment, the memory apparatus 51 stores the magnification at the time of photographing and the reading sampling pitch as the accompanying information, however, the full sampling pitch is previously calculated based on the magnification and the reading sampling pitch, and that full size sampling pitch may be stored as the accompanying information. In such a case, even when the full size sampling pitch is not calculated one by one at the time of conversion of the image data, the magnification and reduction ratio can be calculated from the full size sampling pitch and a predetermined resolving power which are stored in the accompanying information. Hereupon, as the accompanying information, at least one of the magnification and the reading sampling pitch, and the full size sampling pitch may be stored. Then, in the above example, the magnification is changed, however, when the full size sampling pitch is stored in the accompanying information, the full size sampling pitch may be changed, being adjusted to the predetermined resolving power at the time of conversion. Particularly, when the information at the time of photographing is desired to be remained, it is preferable that the full size sampling pitch is stored together with the magnification and the reading sampling pitch.

Further, in the present embodiment, the image file control apparatus 50 is an exclusive apparatus which controls the image file, however, the image input apparatus or image output apparatus itself may control the image file.

Further, in the present embodiment, the memory circuit 511 is exemplified as the recording medium to record the image file, however, any recording medium when it can record the program, can be applied. For example, as the recording medium, a compact flash (registered trade name), memory stick, smart media, multi-media card, floppy (registered trade name) disk, photo-magnetic recording medium (MO), or CD-R are listed.

According to the invention written in the item 1, when the memory apparatus records the image data, because at least one of the magnification at the time of photographing, and reading sampling pitch at the time of image reading, and full size sampling pitch calculated from the magnification and reading sampling pitch, is stored as the accompanying information, when this accompanying information is made the standard at the time of conversion of the image data, even when many times of the size conversion are not conducted, the image can be displayed in the intended size, and resolving power. In this manner, because the number of times of the size conversion of the image data can be suppressed, the deterioration of the image data can be reduced.

Then, even when the image data obtained in each of the absorption contrast image photographing (normal photographing mode) and the phase contrast image photographing (phase image photographing mode) are mixed, because at least one of the magnification at the time of photographing, and the reading sampling pitch at the time of image reading, and the full size sampling pitch calculated from the magnification and the reading sampling pitch is recorded as the accompanying information, the image data obtained by the different photographing method can be controlled in the same manner, and the control of the image file can be effectively conducted.

According to the invention written in the item 2, because the resolving power conversion apparatus calculates the magnification and reduction ratio at the time of the conversion from the full size sampling pitch, the image data can be converted corresponding to the full size. Hereupon, even when the full size sampling pitch is the image data which is not stored as the accompanying information, because, in the image data, the magnification ratio at the time of the photographing and the reading sampling pitch at the time of the image reading are stored as the accompanying information, the full size sampling pitch can be calculated on the base of the magnification ratio and the reading sampling pitch.

According to the invention written in the item 3, when the resolving power conversion apparatus converts the image data into the predetermined resolving power, because it makes the full size sampling pitch correspond to the predetermined resolving power, also after the conversion, the full size sampling pitch corresponded to the conversion as the accompanying information can be stored. Therefore, when it is converted again, the magnification and reduction ratio can be calculated on the base of this full size sampling pitch.

According to the invention written in the item 4, because the resolving power conversion apparatus converts the image data on the base of the magnification and reduction ratio calculated so as to be a predetermined resolving power, the image file can be controlled under the condition that the image data is converted into a predetermined resolving power.

According to the invention written in the item 5, because the resolving power conversion apparatus converts the image data on the base of the magnification and reduction ratio calculated so as to be the resolving power in which the magnification ratio is a full size, the image file can be controlled under the condition that the image data is converted into the full size.

According to the invention written in the item 6, because the data output apparatus outputs the image data stored in the memory apparatus to the image output apparatus, the image data controlled in the image file control apparatus can be outputted by the image output apparatus.

According to the invention written in the item 7, because the resolving power conversion apparatus converts the image data based on the magnification and reduction ratio calculated so as to be the resolving power which is required by the image output apparatus, the image file can be controlled under the condition that the image data is converted into the resolving power required by the image output apparatus.

According to the invention written in the item 8, because, when the data output apparatus outputs the image data, it outputs the image data together with also the accompanying information, even by the image output apparatus, according to the accompanying information, the image data can be converted.

According to the invention written in the item 9, because the resolving power conversion apparatus converts the image data based on the magnification and reduction ratio calculated so as to be a predetermined resolving power, before the output of the data output apparatus, the image data is converted from the condition at the time of the storing, and can be outputted.

According to the invention written in the item 10, because the resolving power conversion apparatus converts the image data based on the magnification and reduction ratio calculated so as to be a resolving power in which the magnification ratio becomes a full size, before the output of the data output apparatus, it can convert the image data into a resolving power in which the magnification ratio becomes a full size, from the condition at the time of storing, and output it.

According to the invention written in the item 11, because the resolving power conversion apparatus converts the image data based on the magnification and reduction ratio calculated so as to be a resolving power which is required by the image output apparatus, before the output of the data output apparatus, it can convert the image data into a resolving power which is required by the image output apparatus, from the condition at the time of the storing, and output it.

What is claimed is:

1. An image file storing and outputting system comprising:
    an image data storing apparatus for storing plural sets of raw image data together with respective supplemental information for each of the plural sets of raw image data, wherein each set of raw image data comprises raw image data output by an image reading device, which obtains the raw image data by reading, with a sampling pitch, a radiation image obtained by radiographing, with a magnification, a body part of a patient having an ID code by one of an absorption contrast radiography and a phase contrast radiography, and wherein the supplemental information comprises the ID code of the patient corresponding to the raw image data, and at least one of: a set of information including the magnification of the radiographing and the sampling pitch with which the radiation image was read by the image reading device, and a full size sampling pitch calculated based on the set of information;
    a resolving power conversion apparatus for converting one of the sets of raw image data stored in the image data storing apparatus based on a predetermined resolving power and the supplemental information attached to the set of raw image data;

an input apparatus, which is connected to the resolving power conversion apparatus, for inputting the predetermined resolving power; and an image output apparatus for outputting an image based on the converted image data converted by the resolving power conversion apparatus.

2. The system according to claim 1, wherein the image output apparatus comprises a display.

3. The system according to claim 1, wherein the image output apparatus comprises a printer.

4. The system according to claim 1, wherein the resolving power conversion apparatus converts the raw image data to the predetermined resolving power, and a magnification/reduction ratio at a time of conversion is calculated from the full size sampling pitch.

5. The system according to claim 4, wherein the resolving power conversion apparatus converts the raw image data based on the calculated magnification/reduction ratio.

6. The system according to claim 5, wherein the resolving power conversion apparatus converts the raw image data based on the calculated magnification/reduction ratio so that the magnification becomes a full size.

* * * * *